(12) United States Patent
Reevell

(10) Patent No.: US 10,842,954 B2
(45) Date of Patent: Nov. 24, 2020

(54) AEROSOL-GENERATING SYSTEM HAVING A CARTRIDGE WITH A SIDE APERTURE

(71) Applicant: Altria Client Services LLC, Richmond, VA (US)

(72) Inventor: Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 177 days.

(21) Appl. No.: 15/846,656

(22) Filed: Dec. 19, 2017

(65) Prior Publication Data

US 2018/0169357 A1 Jun. 21, 2018

Related U.S. Application Data

(63) Continuation of application No. PCT/EP2017/080877, filed on Nov. 29, 2017.

(30) Foreign Application Priority Data

Dec. 19, 2016 (EP) .................................... 16205110

(51) Int. Cl.
*A61M 15/06* (2006.01)
*A61M 11/04* (2006.01)
*A24F 47/00* (2020.01)

(52) U.S. Cl.
CPC ........... *A61M 15/06* (2013.01); *A24F 47/008* (2013.01); *A61M 11/042* (2014.02);
(Continued)

(58) Field of Classification Search
None
See application file for complete search history.

(56) References Cited

U.S. PATENT DOCUMENTS 4,655,229 A * 4/1987 Sensabaugh, Jr. .... A24F 47/002
131/273
2008/0092912 A1 4/2008 Robinson et al.
(Continued)

FOREIGN PATENT DOCUMENTS

EP 2959784 A1 12/2015
EP 3275321 A1 1/2018
(Continued)

OTHER PUBLICATIONS

Third Party Observation dated Feb. 7, 2020 for corresponding European Application No. 17804211.5.
(Continued)

*Primary Examiner* — Joseph M. Pelham
(74) *Attorney, Agent, or Firm* — Harness, Dickey & Pierce, P.L.C.

(57) ABSTRACT

An aerosol-generating system includes a cartridge and an aerosol-generating device configured to receive the cartridge. The cartridge includes a cartridge housing and a cartridge aerosol-forming substrate within the cartridge housing. The cartridge housing has a first end, a second end, a first side between the first end and the second end, and at least one aperture on the first side. The aerosol-generating device includes a device housing, a liquid aerosol-forming substrate, an electric heater, a power supply, and a controller. The device housing defines a cavity, a cavity air inlet, and a cavity air outlet. The cavity is configured to receive the cartridge such that an airflow from the cavity air inlet to the cavity outlet flows through the cartridge via the at least one aperture during an operation of the aerosol-generating system.

13 Claims, 9 Drawing Sheets

(52) U.S. Cl.
CPC . *A61M 2205/121* (2013.01); *A61M 2205/123* (2013.01); *A61M 2205/3653* (2013.01); *A61M 2205/50* (2013.01); *A61M 2205/8206* (2013.01)

(56) References Cited

U.S. PATENT DOCUMENTS

| | | | |
|---|---|---|---|
| 2013/0014772 A1 | 1/2013 | Liu | |
| 2013/0333700 A1 | 12/2013 | Buchberger | |
| 2016/0073695 A1 | 3/2016 | Sears et al. | |
| 2018/0027882 A1* | 2/2018 | Hepworth | A61M 11/041 |
| 2018/0132534 A1* | 5/2018 | Reevell | A61M 15/06 |
| 2018/0132535 A1* | 5/2018 | Reevell | H05B 3/44 |
| 2018/0168228 A1* | 6/2018 | Reevell | A24F 47/008 |
| 2018/0168230 A1* | 6/2018 | Reevell | A24F 47/008 |
| 2018/0168231 A1* | 6/2018 | Reevell | A61M 15/0003 |
| 2018/0169355 A1* | 6/2018 | Reevell | A61M 15/0036 |
| 2018/0338531 A1* | 11/2018 | Reevell | A61M 15/00 |

FOREIGN PATENT DOCUMENTS

| | | |
|---|---|---|
| WO | WO-2015/179388 A1 | 11/2015 |
| WO | WO-2016/014652 A1 | 1/2016 |
| WO | WO-2016/121143 A1 | 8/2016 |
| WO | WO-2016/159013 A1 | 10/2016 |

OTHER PUBLICATIONS

Extended European Search Report for European Application No. 16205110.6 dated Jun. 7, 2017.
www.reuters.com/article/us-brit-am-tobacco-products-idUSKCN0T71U020151118<https://protect-us.mimecast.com/s/Jq6bBvC9X01ho> last accessed Dec. 19, 2017.
http://jinjiatech.com/PRODUCTS/Heat/91_<https://protect-us.mimecast.com/s/X8vqBguOLaRfM> last accessed Dec. 19, 2017.
International Search Report and Written Opinion for corresponding Application No. PCT/EP2017/080877 dated Jan. 9, 2018.
International Preliminary Report on Patentability for corresponding PCT Application No. PCT/EP2017/080877 dated Jul. 4, 2019.

* cited by examiner

AEROSOL-GENERATING SYSTEM HAVING A CARTRIDGE WITH A SIDE APERTURE

CROSS-REFERENCE TO RELATED APPLICATIONS

This is a continuation of and claims priority to PCT/EP2017/080877, filed on Nov. 29, 2017, and further claims priority to EP 16205110.6, filed on Dec. 19, 2016, both of which are hereby incorporated by reference in their entirety.

BACKGROUND

Field

Example embodiments relate to an aerosol-generating system (which may also be referred to as an electronic vaping system) comprising a cartridge having at least one aperture in a side of the cartridge.

Description of Related Art

An aerosol-generating system may comprise an aerosol-generating device comprising a battery, control electronics, and an electric heater for heating an aerosol-forming substrate. The aerosol-forming substrate may be contained within part of the aerosol-generating device. For example, the aerosol-generating device may comprise a liquid storage portion in which a liquid aerosol-forming substrate, such as a nicotine solution, is stored.

Some devices have attempted to include a tobacco-based substrate to impart a tobacco taste to the aerosol. However, such devices exhibit increased complexity in structure and associated manufacturing processes.

SUMMARY

An aerosol-generating system comprises a cartridge and an aerosol-generating device configured to receive the cartridge. The cartridge may include a cartridge housing and a cartridge aerosol-forming substrate within the cartridge housing. The cartridge housing has a first end, a second end, and a cartridge axis extending between the first end and the second end. The cartridge housing defines at least one aperture between the first end and the second end. The aerosol-generating device may include a device housing, a liquid storage section, an electric heater, and a power supply section. The device housing defines a cavity, a cavity air inlet, and a cavity air outlet. The cavity is configured to receive the cartridge. The cavity air inlet is at an upstream end of the cavity, and the cavity air outlet is at a downstream end of the cavity such that an airflow from the cavity air inlet to the cavity air outlet passes through the cartridge via the at least one aperture. The liquid storage section may include a liquid aerosol-forming substrate. The electric heater is configured to heat the liquid aerosol-forming substrate from the liquid storage section. The power supply section includes a power supply and a controller configured to control a supply of electrical power from the power supply to the electric heater.

The cartridge includes a first side and an opposing second side between the first end and the second end. The cartridge aerosol-forming substrate is between the first side and the second side. The at least one aperture may comprise a first aperture on the first side.

The first side may have a length parallel to the cartridge axis, and the first aperture may extend along less than 50 percent of the length of the first side.

The at least one aperture may further comprise a second aperture on the first side of the cartridge and spaced apart from the first aperture. The first aperture may be proximate to the first end of the cartridge housing, and the second aperture may be proximate to the second end of the cartridge housing.

The aerosol-generating device may further comprise an airflow blocking element extending inward from a sidewall of the device housing defining the cavity so as to be between the first aperture and the second aperture when the cartridge is received within the cavity. The airflow blocking element may be configured to direct the airflow from the cavity air inlet through the first aperture, across at least a portion of the cartridge aerosol-forming substrate, and through the second aperture to the cavity air outlet during an operation of the aerosol-generating system.

The at least one aperture may further comprises a second aperture on the second side of the cartridge. The first aperture may be proximate to the first end of the cartridge housing, and the second aperture may be proximate to the second end of the cartridge housing.

The first side may have a length parallel to the cartridge axis, and the first aperture may extend along at least 50 percent of the length of the first side.

The at least one aperture may consist of the first aperture as a sole aperture defined by the cartridge housing.

The airflow blocking element may be configured to direct the air flow from the cavity air inlet through the first aperture, across at least a portion of the cartridge aerosol-forming substrate, and back through the first aperture to the cavity air outlet during an operation of the aerosol-generating system.

The second side may have a length parallel to the cartridge axis, and the second aperture may extend along at least 50 percent of the length of the second side. The second aperture may at least partially overlap the first aperture.

The cartridge housing may define a plurality of substrate compartments, and the cartridge aerosol-forming substrate may be positioned within at least one of the plurality of substrate compartments. The plurality of substrate compartments may be between the first aperture and the second aperture.

The at least one airflow blocking element may be configured to direct the airflow from the cavity air inlet along a serpentine path passing through each of the plurality of substrate compartments via the first and second apertures to the cavity air outlet during an operation of the aerosol-generating system.

The cartridge housing may include a curved wall portion defining the second side of the cartridge.

The first end of the cartridge housing may extend at a non-perpendicular angle with respect to the cartridge axis. The cartridge and the aerosol-generating device may be configured so that a portion of the first end of the cartridge housing abuts an upstream end wall of the cavity when the cartridge is received within the cavity so that the first end of the cartridge housing directs the airflow from the cavity air inlet to the first side of the cartridge.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
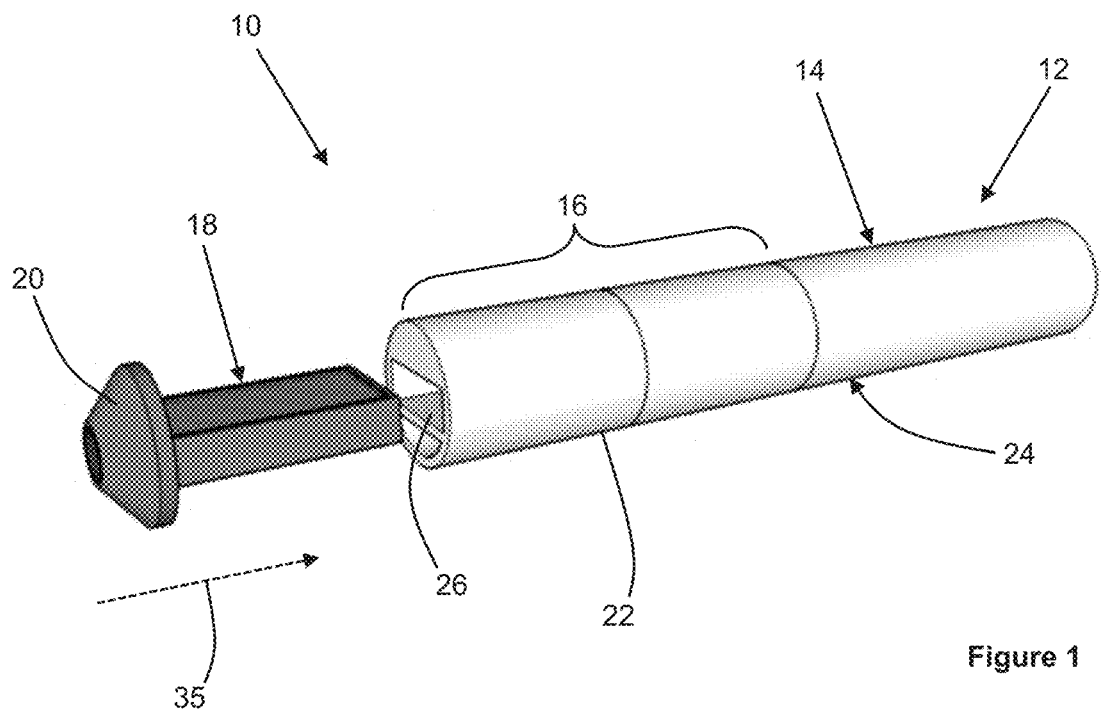
FIG. 1 is a perspective view of an aerosol-generating system according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as controllers, processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to an example embodiment, there is provided an aerosol-generating system (which may also be referred to as an electronic vaping system) comprising a cartridge and an aerosol-generating device. The cartridge comprises a cartridge housing and a cartridge aerosol-forming substrate positioned within the cartridge housing. The cartridge housing has a first end and a second end and defines a cartridge axis extending between the first end and the second end. The cartridge housing further defines at least one aperture positioned on a first side of the cartridge between the first end and the second end of the cartridge housing. The aerosol-generating device comprises a cavity for receiving at least a portion of the cartridge, a cavity air inlet at an upstream end of the cavity and a cavity air outlet at a downstream end of the cavity, wherein the aerosol-generating system is configured for insertion of the cartridge into the cavity along a first direction parallel to the cartridge axis. The aerosol-generating device further comprises a liquid storage section comprising a liquid aerosol-forming substrate positioned within the liquid storage section, an electric heater configured to heat liquid aerosol-forming substrate from the liquid storage section during use of the aerosol-generating system, and a power supply section. The power supply section comprises a power supply and a controller for controlling a supply of electrical power from the power supply to the electric heater. The aerosol-generating system is configured so that, when the cartridge is received within the cavity, the cartridge housing and the aerosol-generating device cooperate to direct airflow from the cavity air inlet through the at least one aperture defined by the cartridge housing so that airflow from the cavity air inlet to the cavity air outlet flows through the cartridge.

An aerosol-forming substrate or a pre-vapor formulation may be used in connection with the systems and methods described herein. As used herein, the term "aerosol-forming substrate" is used to describe a substrate capable of releasing volatile compounds, which can form an aerosol. The aerosols generated from aerosol-forming substrates of aerosol-generating systems according to the non-limiting embodiments herein may be visible or invisible and may include vapours (for example, fine particles of substances, which are in a gaseous state, that are ordinarily liquid or solid at room temperature) as well as gases and liquid droplets of condensed vapours. A "pre-vapor formulation" is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol.

Aerosol-generating systems according to the non-limiting embodiments herein are configured to direct airflow through the cartridge via at least one aperture on a side of the cartridge. Providing the at least one aperture on a side of the cartridge can facilitate improved airflow through the aerosol-generating system. For example, one or more condensing chambers can be provided coaxially with the cartridge, which may shorten the length of the aerosol-generating system compared to known systems in which a cartridge is configured for airflow through apertures on the ends of the cartridge.

Providing the at least one aperture on a side of the cartridge can facilitate an increase in the size of the at least one aperture compared to known systems in which an airflow aperture is provided in an end of the cartridge. A larger aperture can facilitate filling of the cartridge with the cartridge aerosol-forming substrate. A larger aperture can increase the cross-sectional area of the cartridge for airflow entering the cartridge, which may reduce the resistance to draw of the aerosol-generating system. An increased flow area may also facilitate a reduced thickness of the cartridge aerosol-generating substrate compared to known systems, which may further reduce the resistance to draw.

The aerosol-generating system may comprise at least one system airflow inlet and at least one system airflow outlet.

During use, air flows through the aerosol-generating system along a flow path from the system airflow inlet to the system airflow outlet. Air flows along the flow path from an upstream end of the flow path at the system airflow inlet to a downstream end of the flow path at the system airflow outlet.

The cartridge may comprise a second side opposite the first side, wherein the cartridge aerosol-forming substrate is positioned between the first side and the second side. The at least one aperture may comprise a first aperture extending across at least a portion of the first side of the cartridge.

The first side may have a length extending parallel to the cartridge axis, wherein the first aperture extends along less than about 50 percent of the length of the first side. The first aperture may be positioned proximate the first end of the cartridge housing, the at least one aperture further comprising a second aperture extending across a portion of the first side of the cartridge and spaced apart from the first aperture, the second aperture positioned proximate the second end of the cartridge housing. Providing a first aperture positioned proximate the first end of the cartridge and a second aperture positioned proximate the second end of the cartridge may facilitate airflow through substantially the entire cartridge.

The aerosol-generating device may comprise an airflow blocking element extending from a sidewall of the cavity towards the first side of the cartridge and positioned between the first aperture and the second aperture when the cartridge is received within the cavity. The airflow blocking element is configured so that, in use, the airflow blocking element directs air flow from the cavity air inlet through the first aperture, across at least a portion of the cartridge aerosol-forming substrate, and through the second aperture to the cavity air outlet when the cartridge is received within the cavity. The cartridge housing may define a cartridge wall portion extending between the first aperture and the second aperture, wherein the airflow blocking element is configured to engage the cartridge wall portion when the cartridge is received within the cavity.

The first aperture may be positioned proximate the first end of the cartridge housing and the at least one aperture may further comprise a second aperture extending across a portion of the second side of the cartridge, the second aperture positioned proximate the second end of the cartridge housing. This arrangement may facilitate airflow through substantially the entire cartridge.

The aerosol-generating device may comprise a first airflow blocking element extending from a first sidewall of the cavity towards the first side of the cartridge and positioned downstream of the first aperture when the cartridge is received within the cavity. The aerosol-generating device may comprise a second airflow blocking element extending from a second sidewall of the cavity towards the second side of the cartridge and positioned upstream of the second aperture when the cartridge is received within the cavity. The first and second airflow blocking elements are configured so that, in use, the first airflow blocking element directs air flow from the cavity air inlet through the first aperture, across at least a portion of the cartridge aerosol-forming substrate, and through the second aperture where the second airflow blocking element directs the air flow to the cavity air outlet. The cartridge housing may define a first cartridge wall portion adjacent the first aperture and a second cartridge wall portion adjacent the second aperture, wherein the first airflow blocking element is configured to engage the first cartridge wall portion and the second airflow blocking element is configured to engage the second cartridge wall portion when the cartridge is received within the cavity.

The first side of the cartridge may have a length extending parallel to the cartridge axis, wherein the first aperture extends along at least about 50 percent of the length of the first side. This arrangement may provide a first aperture that is sufficiently large to provide a desirable resistance to draw for the aerosol-generating system. This arrangement may provide a first aperture that is sufficiently large to facilitate filling of the cartridge housing with the cartridge aerosol-forming substrate during manufacture of the cartridge. The first aperture may extend along substantially the entire length of the first side.

The first aperture may be the only aperture defined by the cartridge housing. The aerosol-generating device may comprise an airflow blocking element extending from a sidewall of the cavity towards the first side of the cartridge, the airflow blocking element positioned to direct air flow from the cavity air inlet through the first aperture, across at least a portion of the cartridge aerosol-forming substrate, and back through the first aperture to the cavity air outlet.

In example embodiments in which the first aperture extends along at least about 50 percent of the length of the first side of the cartridge, the at least one aperture may further comprise a second aperture extending across at least a portion of the second side of the cartridge. The second side may have a length extending parallel to the cartridge axis, wherein the second aperture extends along at least about 50 percent of the length of the second side, and wherein the second aperture at least partially overlaps the first aperture. This arrangement may reduce the resistance to draw of the aerosol-generating system by facilitating direct airflow across the cartridge aerosol-forming substrate from the first aperture to the second aperture. The first aperture may extend along substantially the entire length of the first side. The second aperture may extend along substantially the entire length of the second side.

The cartridge housing may define a plurality of substrate compartments, wherein the cartridge aerosol-forming substrate is positioned within at least one of the substrate compartments. The cartridge may comprise a plurality of cartridge aerosol-forming substrates, wherein each cartridge aerosol-forming substrate is positioned within one of the substrate compartments. The plurality of cartridge aerosol-forming substrates may be different from each other, or they may be the same.

At least one of the substrate compartments may not contain a cartridge aerosol-forming substrate. At least one of the substrate compartments may contain a filter material. The filter material may comprise cellulose acetate. At least one of the substrate compartments may contain a flavourant. The flavourant may comprise menthol.

In a non-limiting embodiment, the first aperture overlies a first side of each of the substrate compartments, the at least one aperture further comprising a second aperture extending across at least a portion of the second side of the cartridge, the second aperture overlying a second side of each of the substrate compartments.

The aerosol-generating system may be configured to facilitate parallel flow of air through each of the substrate compartments. The cavity air inlet may be positioned to provide airflow to the first aperture and the cavity air outlet may be positioned to receive airflow from the aperture.

The aerosol-generating system may be configured to facilitate a serial flow of airflow through each of the substrate compartments. The aerosol-generating device may comprise at least one airflow blocking element. The at least one airflow blocking element is positioned within the cavity to direct airflow through each of the substrate compartments when the cartridge is received within the cavity. The at least one airflow blocking element may form part of a device housing. The at least one airflow blocking element may be configured to direct airflow along a serpentine airflow path through the substrate compartments via the first and second apertures during use of the aerosol-generating system.

The at least one airflow blocking element may comprises a set of one or more first airflow blocking elements extending from a first wall of the cavity and a set of one or more second airflow blocking elements extending from a second wall of the cavity opposite the first wall, wherein the first airflow blocking elements are spaced apart along the first wall in the downstream direction and the second airflow blocking elements are spaced apart along the second wall in the downstream direction, and wherein the first airflow blocking elements are offset from the second airflow blocking elements to define a serpentine airflow path through the cavity and substrate compartments when the cartridge assembly is received within the cavity.

Defining a serpentine flow path may ensure that airflow through the aerosol-generating system flows through each substrate compartment.

As described herein, the cartridge may comprise a second side opposite the first side. In example embodiments in which the at least one aperture comprises only a first aperture positioned on the first side of the cartridge, or first and second apertures positioned on the first side of the cartridge, the cartridge housing may comprise a wall portion defining the second side of the cartridge, wherein the wall portion is curved. Providing a curved wall portion defining the second side of the cartridge may maximise the internal volume of the cartridge, which may increase the amount of the cartridge aerosol-forming substrate that can be positioned within the cartridge. Providing a curved wall portion may provide the cartridge with a rotational asymmetry, which may facilitate insertion of the cartridge into the cavity in the correct orientation.

The first end of the cartridge housing may extend at a non-perpendicular angle with respect to the cartridge axis, wherein the cartridge and the aerosol-generating device are configured so that a portion of the first end of the cartridge housing abuts an upstream end wall of the cavity when the cartridge is received within the cavity so that the first end of the cartridge housing directs airflow from the cavity air inlet to the first side of the cartridge. This arrangement may eliminate the need to provide one or more airflow blocking elements in the cavity, particularly in example embodiments in which the cartridge comprises a single substrate compartment, a first aperture on the first side of the cartridge and a second aperture on a second side of the cartridge.

The aerosol-generating system may comprise a mouthpiece. The mouthpiece may form part of the cartridge. The mouthpiece may be formed separately from the cartridge and configured for attachment to at least one of the cartridge and the vaporiser section, for example by an interference fit. The mouthpiece may comprise a mouthpiece air outlet configured for fluid communication with the cavity air outlet during use. In example embodiments in which the aerosol-generating system comprises at least one system airflow outlet, the mouthpiece air outlet may form a system airflow outlet.

The cartridge may be configured to be retained within the cavity by an interference fit. Each of the cartridge and the cavity may have any suitable cross-sectional shape. A cross-sectional shape of the cartridge may be substantially the same as a cross-sectional shape of the cavity. Suitable cross-sectional shaped include circular, semi-circular, polygonal, such as rectangular, including square, and irregular shapes.

The cartridge housing may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge may comprise a layer of porous material extending across the at least one aperture. In example embodiments in which the at least one aperture comprises a first aperture, the layer of porous material may comprise a first layer of porous material extending across the first aperture. In example embodiments in which the at least one aperture comprises a second aperture, the layer of porous material may comprise a second layer of porous material extending across the first aperture. The one or more layers of porous material may retain the cartridge aerosol-forming substrate within the cartridge and also allow airflow through the cartridge. Each layer of porous material may comprise a mesh.

The cartridge aerosol-forming substrate may comprise a solid aerosol-forming substrate. The solid aerosol-forming substrate may comprise tobacco. The solid aerosol-forming substrate may comprise a tobacco-containing material containing volatile tobacco flavour compounds which are released from the substrate upon heating.

The solid aerosol-forming substrate may comprise tobacco containing deprotonated nicotine. Deprotonating the nicotine within tobacco may increase the volatility of the nicotine. Nicotine may be deprotonated by subjecting the tobacco to an alkalising treatment.

The solid aerosol-forming substrate may comprise a non-tobacco material. The solid aerosol-forming substrate may comprise tobacco-containing material and non-tobacco containing material.

The solid aerosol-forming substrate may include at least one aerosol-former. As used herein, the term 'aerosol former' is used to describe any suitable known compound or mixture of compounds that, in use, facilitates formation of an aerosol. Suitable aerosol-formers include, but are not limited to: polyhydric alcohols, such as propylene glycol, triethylene glycol, 1,3-butanediol, and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

In an example embodiment, the aerosol formers are polyhydric alcohols or mixtures thereof, such as propylene glycol, triethylene glycol, 1,3-butanediol, and glycerine.

The solid aerosol-forming substrate may comprise a single aerosol former. Alternatively, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content of between approximately 5 percent and approximately 30 percent on a dry weight basis.

The solid aerosol-forming substrate may have an aerosol former content of approximately 20 percent on a dry weight basis.

The liquid aerosol-forming substrate of the liquid storage section may comprise a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. The liquid aerosol-forming substrate may comprise an aerosol former. Suitable aerosol formers include polyhydric alcohols or mixtures thereof, such as propylene glycol, triethylene glycol, 1,3-butanediol, and glycerine.

The liquid aerosol-forming substrate in the liquid storage section may comprise nicotine.

The liquid aerosol-forming substrate may be free from nicotine. In such example embodiments, the vaporised liquid aerosol-forming substrate may be drawn through a solid aerosol-forming substrate of one of the cartridges, during use, to strip one or more volatile compounds from the solid aerosol-forming substrate. The vaporised liquid aerosol-forming substrate may strip nicotine from the solid-aerosol-forming substrate. A cartridge having a solid aerosol-forming substrate comprising tobacco containing deprotonated nicotine may be particularly suited to embodiments in which the liquid aerosol-forming substrate is free from nicotine.

The liquid storage section may comprise a porous carrier material, wherein the liquid aerosol-forming substrate is provided on the porous carrier material. Providing the liquid aerosol-forming substrate on a porous carrier material may reduce the risk of the liquid aerosol-forming substrate leaking from the liquid storage section.

The porous carrier material may comprise any suitable material or combination of materials which is permeable to the liquid aerosol-forming substrate and allows the liquid aerosol-forming substrate to migrate through the porous carrier material. The material or combination of materials is inert with respect to the liquid aerosol-forming substrate. The porous carrier material may or may not be a capillary material. The porous carrier material may comprise a hydrophilic material to improve distribution and spread of the liquid aerosol-forming substrate. This may assist with consistent aerosol formation. The particular material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous carrier material may have any suitable porosity so as to be used with different liquid physical properties.

The cartridge aerosol-forming substrate may comprise a liquid aerosol-forming substrate. The liquid aerosol-forming substrate may be provided on a porous carrier material positioned within the cartridge. Suitable liquid aerosol-forming substrates include those described herein with respect to the liquid storage section of the aerosol-generating device. Suitable porous carrier materials include those described herein with respect to the liquid storage section of the aerosol-generating device. The liquid aerosol-forming substrate provided in the cartridge may be different from the liquid aerosol-forming substrate provided in the liquid storage section of the aerosol-generating device.

In example embodiments in which the cartridge aerosol-forming substrate comprises a plurality of cartridge aerosol-forming substrates positioned within a plurality of substrate compartments, at least two of the aerosol-forming substrates may comprise different aerosol-forming substrates. One of the cartridge aerosol-forming substrates may comprise a solid aerosol-forming substrate as described herein. One of the cartridge aerosol-forming substrates may comprise a liquid aerosol-forming substrate as described herein.

The cartridge may comprise a seal extending over the at least one aperture. In example embodiments in which the at least one aperture comprises a first aperture, the seal may comprise a first seal extending across the first aperture. In example embodiments in which the at least one aperture comprises a second aperture, the seal may comprise a second seal extending across the first aperture. Each seal may be a removable seal. Before inserting the cartridge into the cavity, each seal is removed from the cartridge.

Each seal may be secured to the cartridge housing about a periphery of the seal. Each seal may be secured to the cartridge housing by at least one of an adhesive and a weld, such as an ultrasonic weld.

Each seal may be formed from a sheet material. The sheet material may comprise at least one of a polymeric film and a metallic foil.

The aerosol-generating system may further comprise a liquid transfer element configured so that, in use, liquid aerosol-forming substrate is transported by capillary action along the liquid transfer element from the liquid storage section to the electric heater. In example embodiments in which the liquid storage section comprises a porous carrier material, the liquid transfer element is configured to transport liquid aerosol-forming substrate from the porous carrier material to the electric heater.

The liquid transfer element may comprise any suitable material or combination of materials which is able to convey the liquid aerosol-forming substrate along its length. The liquid transfer element may be formed from a porous material, but this need not be the case. The liquid transfer element may be formed from a material having a fibrous or spongy structure. The liquid transfer element may comprise a bundle of capillaries. For example, the liquid transfer element may comprise a plurality of fibres or threads or other fine bore tubes. The liquid transfer element may comprise sponge-like or foam-like material. The structure of the liquid transfer element may form a plurality of small bores or tubes, through which the liquid aerosol-forming substrate can be transported by capillary action. The particular material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres, ceramic, glass fibres, silica glass fibres, carbon fibres, metallic fibres of medical grade stainless steel alloys such as austenitic 316 stainless steel and martensitic 440 and 420 stainless steels. The liquid transfer element may have any suitable capillarity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the liquid transfer element. The liquid transfer element may be formed from heat-resistant material. The liquid transfer element may comprise a plurality of fibre strands. The plurality of fibre strands may be generally aligned along a length of the liquid transfer element.

In example embodiments in which the liquid storage section comprises a porous carrier material, the porous carrier material and the liquid transfer element may comprise the same material. The porous carrier material and the liquid transfer element may comprise different materials.

The electric heater may be provided separately from one or both of the liquid storage section and the power supply section. The liquid storage section, the electric heater and, where present, the liquid transfer element may be provided together in a vaporiser section. The vaporiser section may comprise a vaporiser housing forming part of a device housing, wherein the vaporiser housing comprises an upstream end configured for connection to the power supply section and a downstream end defining a cavity configured to receive the cartridge assembly. Providing the liquid storage section, the electric heater and, where present, the liquid transfer element in a single vaporiser section separate from the power supply section may facilitate replacement of the vaporiser section (for example, when the liquid aerosol-forming substrate has been depleted) without the need to replace the power supply section.

The electric heater may comprise a resistive heating coil.

The electric heater may comprise a resistive heating mesh.

The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction.

The electrically conductive filaments may define interstices between the filaments and the interstices may have a width of between about 10 micrometres and about 100 micrometres. The filaments give rise to capillary action in the interstices, so that in use, liquid aerosol-forming substrate is drawn into the interstices, increasing the contact area between the heater assembly and the liquid.

The electrically conductive filaments may form a mesh of size between about 160 Mesh US and about 600 Mesh US (+/−10%) (that is, between about 160 and about 600 filaments per inch (+/−10%)). The width of the interstices may be between about 75 micrometres and about 25 micrometres. The percentage of open area of the mesh, which is the ratio of the area of the interstices to the total area of the mesh may be between about 25 percent and about 56 percent. The mesh may be formed using different types of weave or lattice structures. The electrically conductive filaments may be an array of filaments arranged parallel to one another.

The electrically conductive filaments may have a diameter of between about 8 micrometres and about 100 micrometres (e.g., between about 8 micrometres and about 50 micrometres, between about 8 micrometres and about 39 micrometres).

The resistive heating mesh may cover an area of less than or equal to about 25 square millimetres. The resistive heating mesh may be rectangular. The resistive heating mesh may be square. The resistive heating mesh may have dimensions of about 5 millimetres by about 2 millimetres.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Suitable materials for the electrically conductive filaments are 304, 316, 304L, and 316L stainless steel, and graphite.

The electrical resistance of the resistive heating mesh may be between about 0.3 and about 4 Ohms. For example, the electrical resistance of the mesh may be between about 0.5 and about 3 Ohms (e.g., about 1 Ohm).

In example embodiments in which the electric heater comprises a resistive heating coil, the pitch of the coil may be between about 0.5 millimetres and about 1.5 millimetres (e.g., about 1.5 millimetres). The pitch of the coil means the spacing between adjacent turns of the coil. The coil may comprise fewer than six turns (e.g., fewer than five turns). The coil may be formed from an electrically resistive wire having a diameter of between about 0.10 millimetres and about 0.15 millimetres (e.g., about 0.125 millimetres). The electrically resistive wire may be formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. The resistive heating coil may also comprise a metal foil, such as an aluminium foil, which is provided in the form of a ribbon.

The power supply may comprise a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with more than one cartridge assembly.

FIG. 1 shows a perspective view of an aerosol-generating system 10 according to an example embodiment. The aerosol-generating system 10 comprises an aerosol-generating device 12 comprising a power supply section 14 and a vaporiser section 16. The aerosol-generating system 10 further comprises a cartridge 18 and a mouthpiece 20 forming part of the cartridge 18. The vaporiser section 16 comprises a vaporiser housing 22 that forms part of a device housing 24. A downstream end of the vaporiser housing 22 defines a cavity 26 for receiving the cartridge 18.

Figure 2:
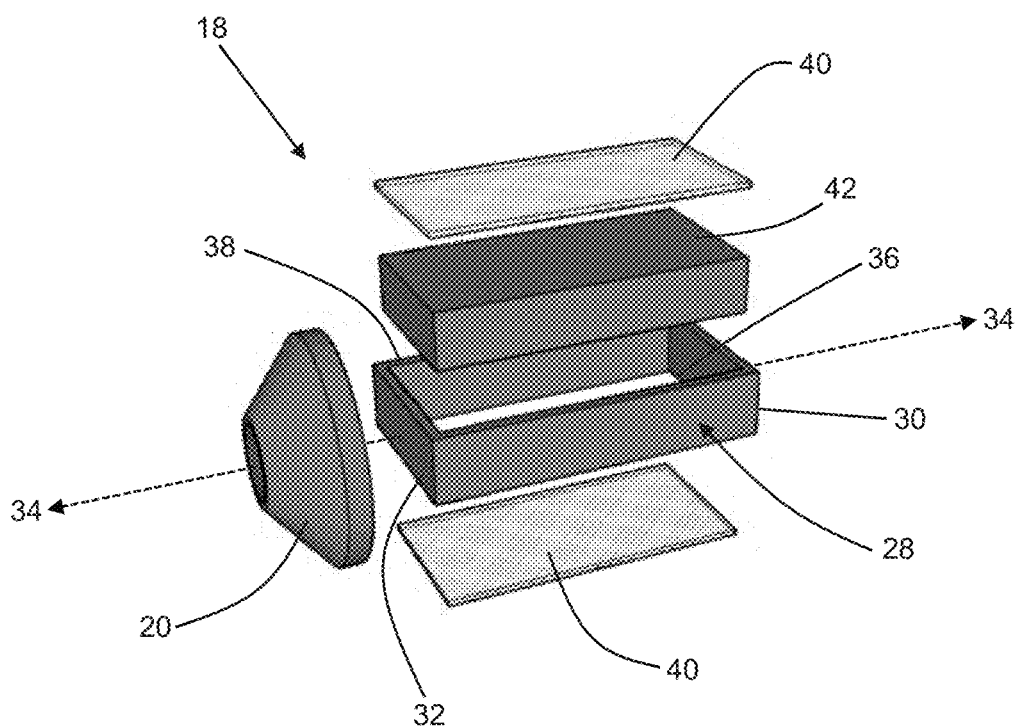
FIG. 2 is an exploded perspective view of the cartridge of the aerosol-generating system of FIG. 1.

FIG. 2 shows an exploded perspective view of the cartridge 18. The cartridge 18 comprises a cartridge housing 28 having a first end 30 and a second end 32, the cartridge housing 28 defining a cartridge axis 34 extending between the first end 30 and the second end 32. The cartridge housing 28 defines a first aperture 36 on a first side of the cartridge 18 and a second aperture 38 on a second side of the cartridge 18, opposite the first side. First and second layers of a porous material 40 in the forms of mesh screens extend across the first and second apertures 36, 38 to retain a cartridge aerosol-forming substrate 42 in the cartridge housing 28.

Figure 3:
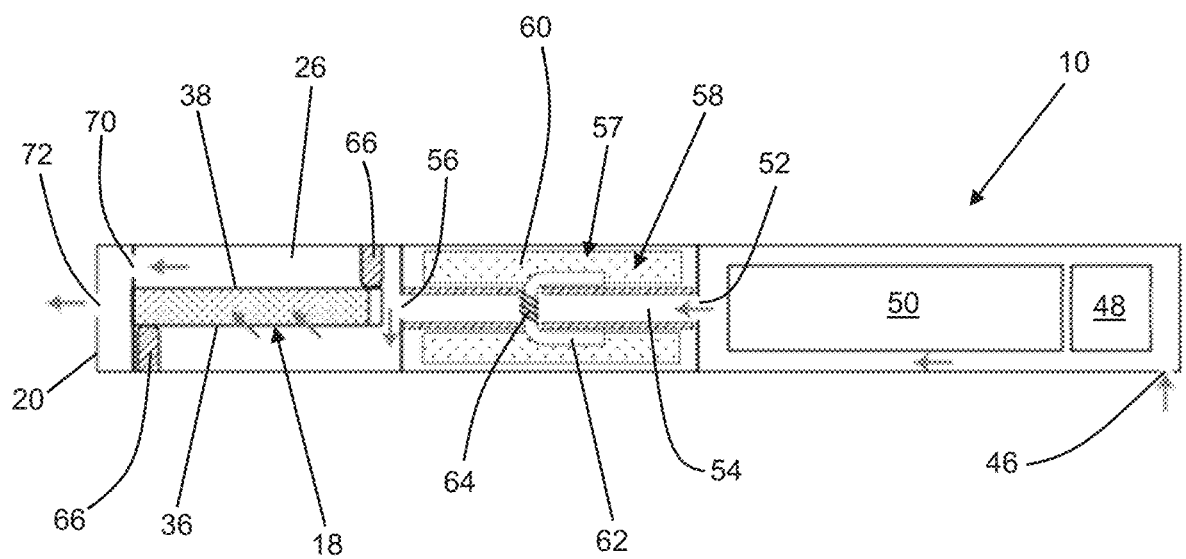
FIG. 3 is a cross-sectional view of the aerosol-generating system of FIG. 1.

FIG. 3 shows a cross-sectional view of the aerosol-generating system 10 with the cartridge 18 received within the cavity 26. The cartridge 18 is inserted into the cavity 26 along a first direction 35 (FIG. 1) that is parallel to the cartridge axis 34.

The power supply section 14 comprises a system air inlet 46 for admitting air into the power supply section 14, a controller 48 and a power supply 50. The controller 48 includes one or more microprocessors, CPUs, SoCs, DSPs, ASICs, FPGAs, computers, or the like, configured as special-purpose machines to perform the functions described herein as well as other well-known functions of the elements.

The vaporiser section 16 comprises a vaporiser air inlet 52 for receiving air from the power supply section 14, an airflow passage 54 in fluid communication with the vaporiser air inlet 52 at its upstream end, and a cavity air inlet 56 providing fluid communication between the downstream end of the airflow passage 54 and the cavity 26.

The vaporiser section 16 further comprises a liquid storage section 57 comprising a liquid aerosol-forming substrate 58 sorbed into an annular porous carrier material 60 positioned outside of the airflow passage 54. A liquid transfer element 62 comprising a capillary wick has first and second ends positioned in contact with the porous carrier material 60 and a central portion positioned within the airflow passage 54. Liquid aerosol-forming substrate 58 is wicked by capillary action along the capillary wick from the porous carrier material 60 to the central portion of the capillary wick.

The vaporiser section 16 also comprises an electric heater 64 comprising a resistive heating coil wound around the central portion of the capillary wick. During operation of the aerosol-generating system 10, the controller 48 controls a supply of electrical energy from the power supply 50 to the electric heater 64 to heat and vaporise liquid aerosol-forming substrate 58 from the central portion of the capillary wick.

The downstream portion of the vaporiser housing 22 defines a plurality of airflow blocking elements 66 extending into the cavity 26. The airflow blocking elements 66 are configured so that, when the cartridge 18 is received within the cavity 26, the airflow blocking elements 66 cooperate with the cartridge 18 to define an airflow path through the cavity 26 and the cartridge 18 via the first and second apertures 36, 38 of the cartridge 18.

At a downstream end of the cavity 26 is a cavity air outlet 70 providing fluid communication between the cavity 26 and the mouthpiece 20. The mouthpiece 20 defines a mouthpiece air outlet 72 for providing an airflow from the aerosol-generating system 10.

During use of the aerosol-generating system 10, air is drawn into the system through the system air inlet 46, through the vaporiser air inlet 52 and into the airflow passage 54 where vaporised liquid aerosol-forming substrate 58 is entrained in the airflow. The airflow then flows through the cavity air inlet 56, into the cavity 26 and the cartridge 18 where volatile compounds from the cartridge aerosol-forming substrate 42 are entrained in the airflow. The airflow then flows out of the cartridge 18 back into the cavity 26, through the cavity air outlet 70 and out of the aerosol-generating system 10 through the mouthpiece air outlet 72 to deliver the vaporised liquid aerosol-forming substrate 58 and the volatile compounds from the cartridge aerosol-forming substrate 42.

Figure 4:
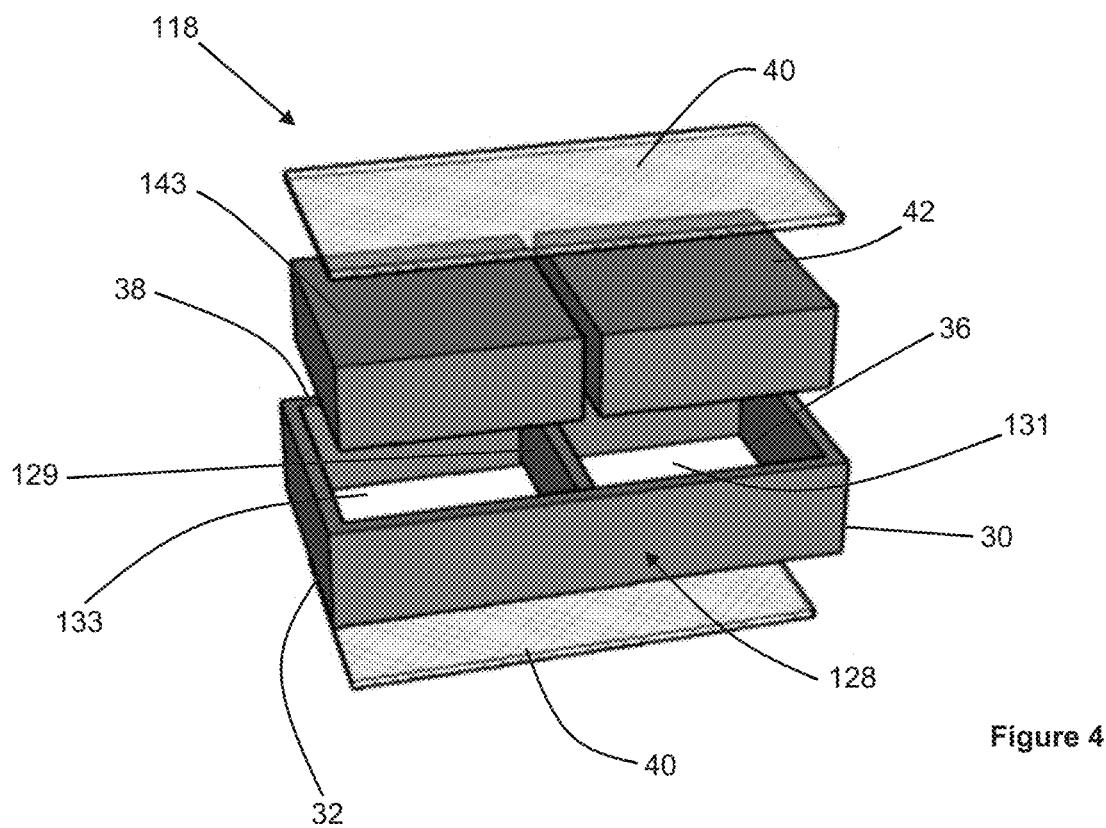
FIG. 4 is an exploded perspective view of another cartridge according to an example embodiment.

FIG. 4 shows an exploded perspective view of a cartridge 118 according to an example embodiment. The cartridge 118 is similar to the cartridge 18 shown in FIGS. 1 to 3 and like reference numerals are used to designate like parts.

Cartridge 118 differs from cartridge 18 by the addition of a dividing wall portion 129 to the cartridge housing 128. The dividing wall portion 129 divides the cartridge into a first substrate compartment 131 and a second substrate compartment 133, the cartridge 118 comprising a first cartridge aerosol-forming substrate 42 positioned within the first substrate compartment 131 and a second cartridge aerosol-forming substrate 143 positioned within the second substrate compartment 133. Otherwise, the construction of the cartridge 118 is the same as the cartridge 18 (the mouthpiece 20 is omitted from FIG. 4 for clarity).

Figure 5:
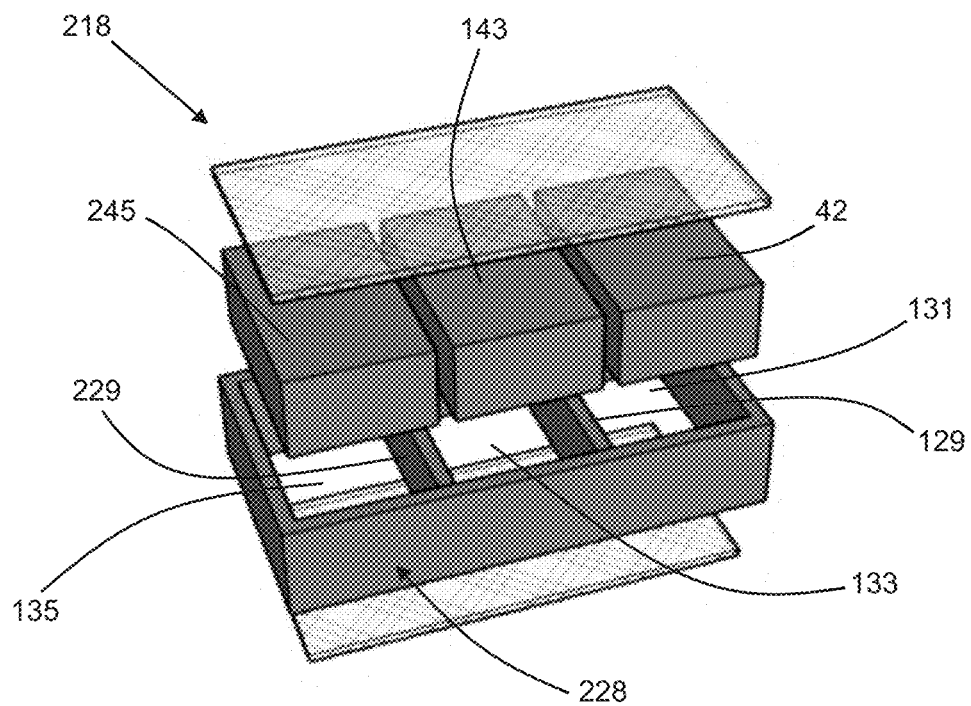
FIG. 5 is an exploded perspective view of another cartridge according to an example embodiment.

FIG. 5 shows an exploded perspective view of a cartridge 218 according to an example embodiment. The cartridge 218 is similar to the cartridge 118 shown in FIG. 4 and like reference numerals are used to designate like parts. The cartridge 218 differs by the addition of a second dividing wall portion 229 to the cartridge housing 228 to create a third substrate compartment 135 in which a third cartridge aerosol-forming substrate 245 is positioned. Otherwise, the construction of the cartridge 218 is the same as the cartridge 118 (the mouthpiece 20 is omitted from FIG. 5 for clarity).

Figure 6:
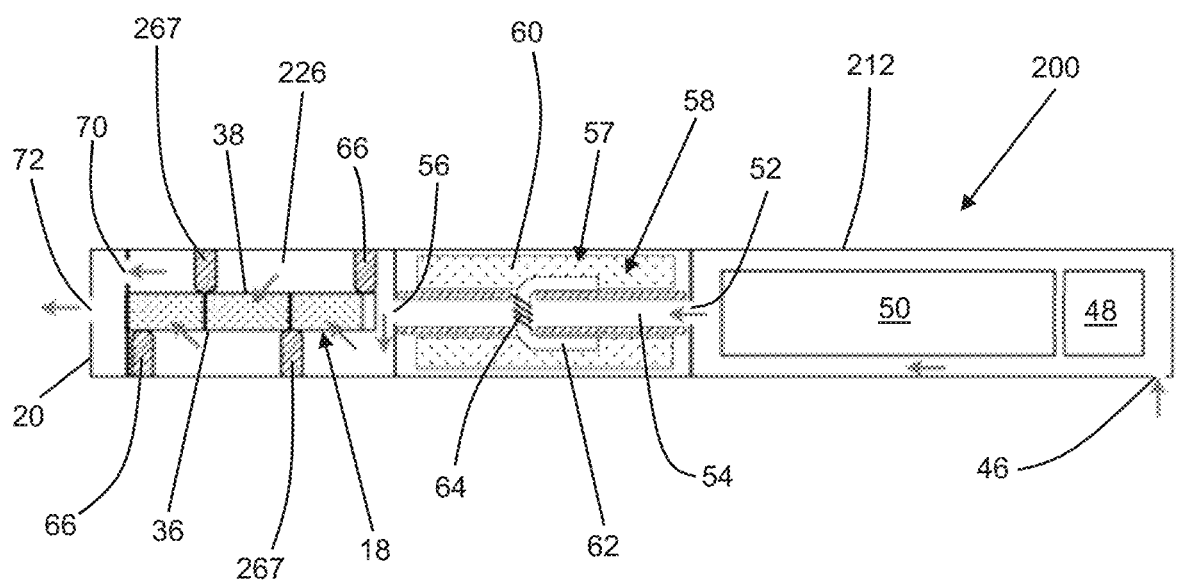
FIG. 6 is a cross-sectional view of an aerosol-generating system comprising the cartridge of FIG. 5.

FIG. 6 shows a cross-sectional view of an aerosol-generating system 200 comprising the cartridge 218 of FIG. 5. The aerosol-generating system 200 is similar to the aerosol-generating system 10 of FIGS. 1 and 3, and like reference numerals are used to designate like parts.

Aerosol-generating system 200 comprises an aerosol-generating device 212 that is substantially the same as the aerosol-generating device 12 of FIGS. 1 and 3, except for the configuration of the cavity 226. In particular, the cavity 226 comprises additional airflow blocking elements 267, wherein the plurality of airflow blocking elements 66, 267 are configured so that, when the cartridge 218 is received within the cavity 226, the airflow blocking elements 66, 267 cooperate with the cartridge 218 to define a serpentine airflow path through the cavity 26 and each of the substrate compartments 131, 133, 135 via the first and second apertures 36, 38 of the cartridge 218.

Figure 7:
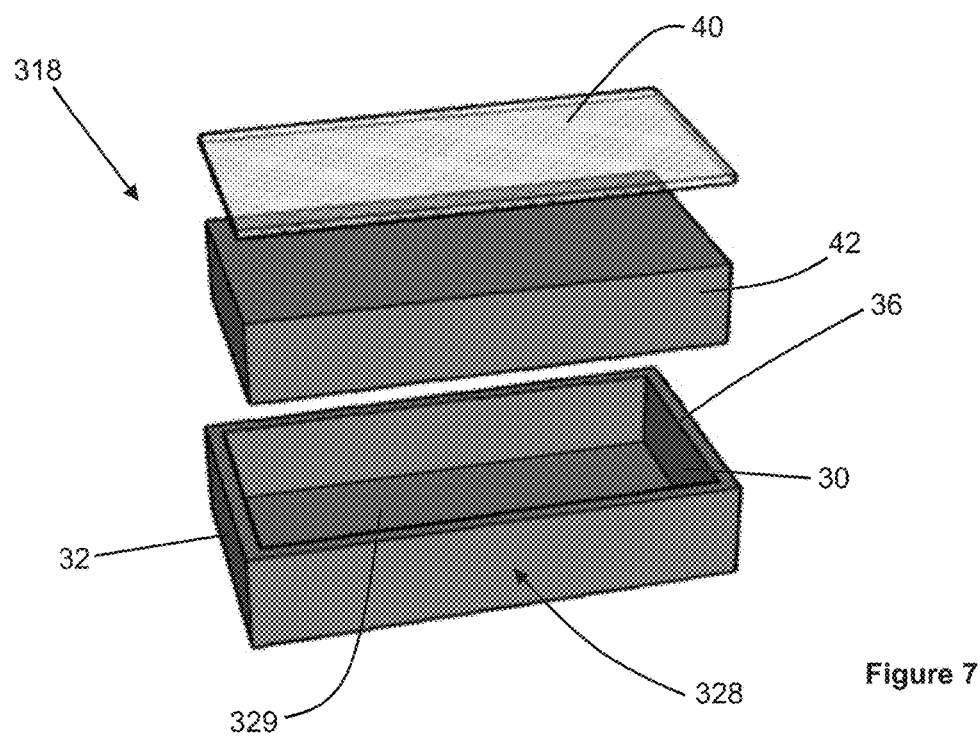
FIG. 7 is an exploded perspective view of a cartridge according to an example embodiment.

FIG. 7 shows an exploded perspective view of a cartridge 318 according to an example embodiment. The cartridge 318 is similar to the cartridge 18 shown in FIGS. 1 to 3 and like reference numerals are used to designate like parts. Cartridge 318 differs by the addition of a wall portion 329 to the second side of the cartridge housing 328 so that the cartridge 318 comprises only a first aperture 36. That is, the cartridge 318 does not comprise a second aperture.

Figure 8:
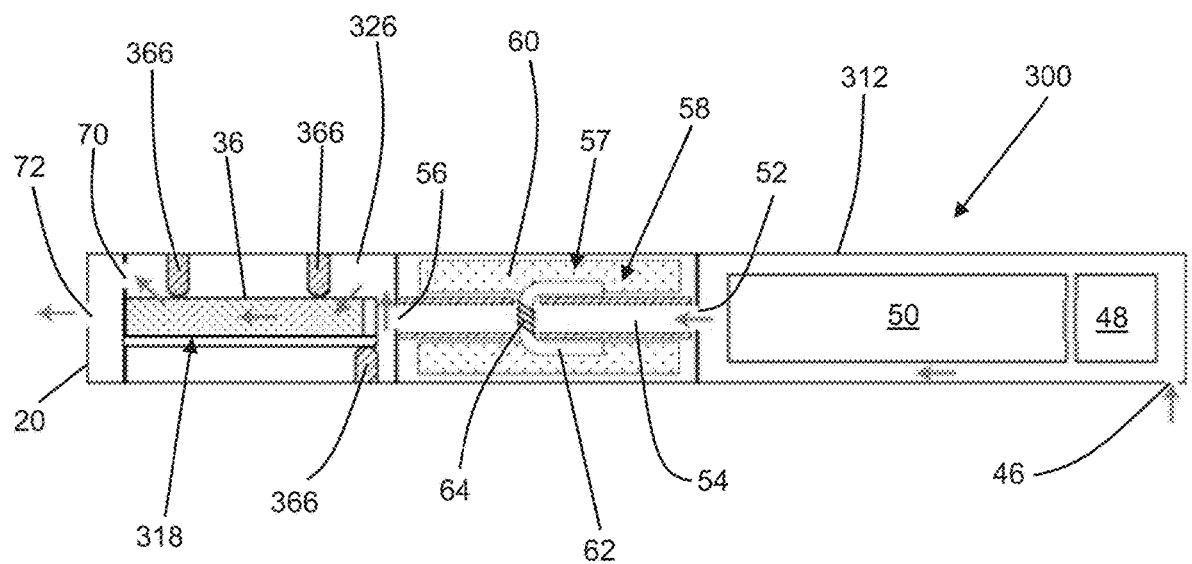
FIG. 8 is a cross-sectional view of an aerosol-generating system comprising the cartridge of FIG. 7.

FIG. 8 shows a cross-sectional view of an aerosol-generating system 300 comprising the cartridge 318 of FIG. 7. The aerosol-generating system 300 is similar to the aerosol-generating system 10 of FIGS. 1 and 3, and like reference numerals are used to designate like parts.

Aerosol-generating system 300 comprises an aerosol-generating device 312 that is substantially the same as the aerosol-generating device 12 of FIGS. 1 and 3, except for the configuration of the cavity 326. In particular, the cavity 326 comprises a different configuration of airflow blocking elements 366 arranged so that, when the cartridge 318 is received within the cavity 326, the airflow blocking elements 366 cooperate with the cartridge 318 to direct airflow into the cartridge 318 through an upstream end of the first aperture 36, and then out of the cartridge 318 through a downstream end of the first aperture 36.

Figure 9:
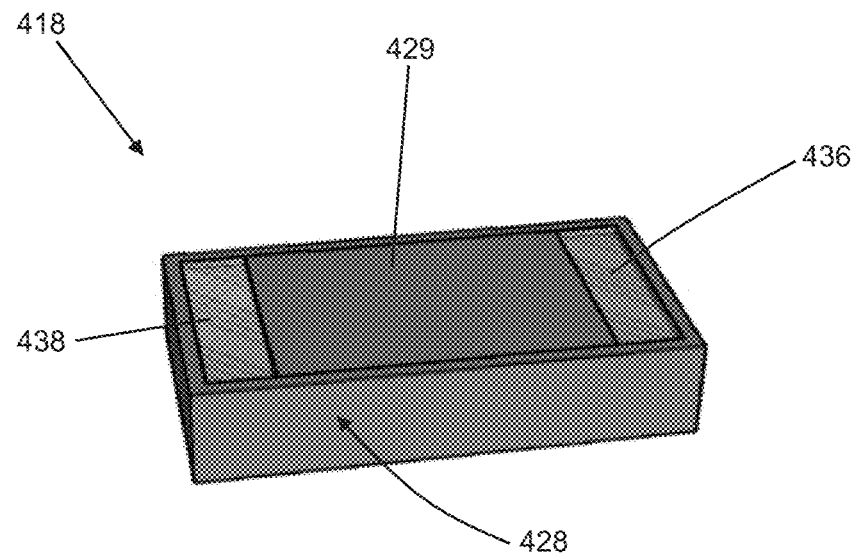
FIG. 9 is a perspective view of another cartridge according to an example embodiment.
Figure 10:
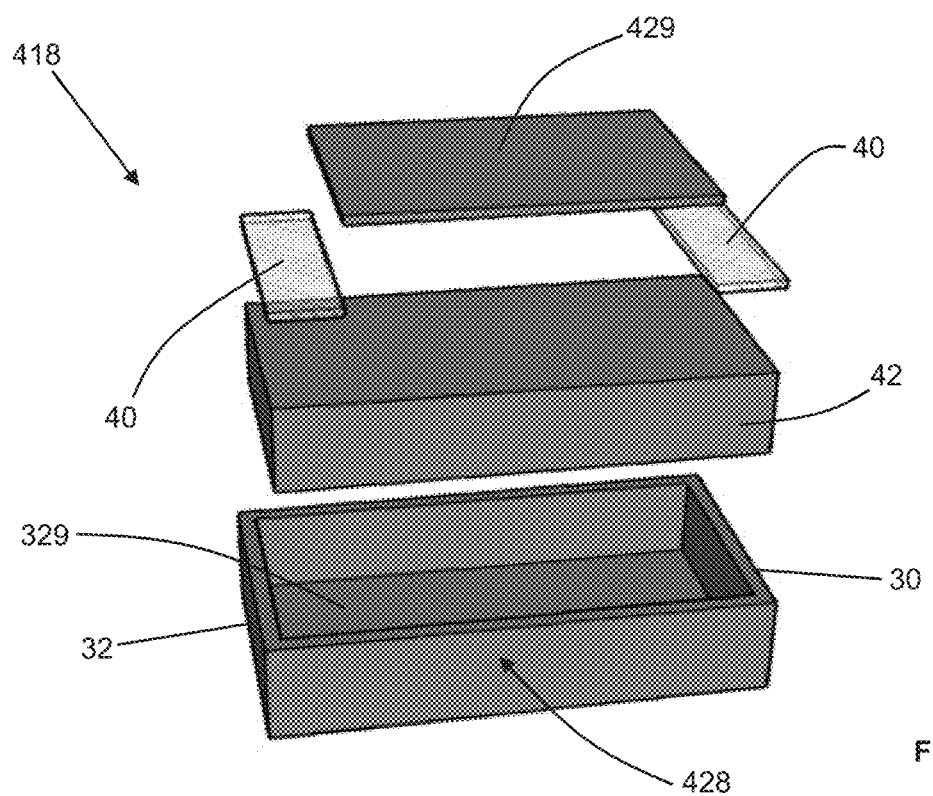
FIG. 10 is an exploded perspective view of the cartridge of FIG. 9.

FIGS. 9 and 10 show a cartridge 418 according to an example embodiment. The cartridge 418 is similar to the cartridge 318 shown in FIG. 7 and like reference numerals are used to designate like parts. Cartridge 418 differs by the addition of a wall portion 429 to the first side of the cartridge housing 428 so that the cartridge 418 comprises a first aperture 436 on the first side of the cartridge 418 and adjacent the first end 30, and a second aperture 438 on the first side of the cartridge 418 and adjacent the second end 32.

Figure 11:
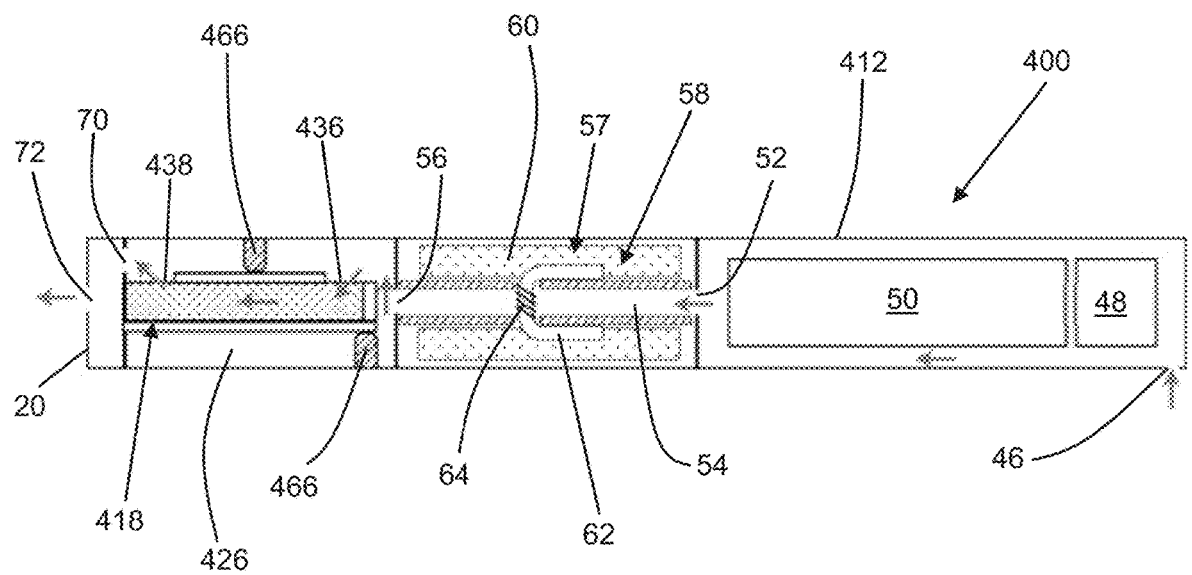
FIG. 11 is a cross-sectional view of an aerosol-generating system comprising the cartridge of FIGS. 9 and 10.

FIG. 11 shows a cross-sectional view of an aerosol-generating system 400 comprising the cartridge 418 of FIGS. 9 and 10. The aerosol-generating system 400 is similar to the aerosol-generating system 300 of FIG. 8, and like reference numerals are used to designate like parts.

Aerosol-generating system 400 comprises an aerosol-generating device 412 that is substantially the same as the aerosol-generating device 312 of FIG. 8, except for the configuration of the cavity 426. In particular, the addition of the wall portion 429 to the first side of the cartridge 418 allows the use of fewer airflow blocking elements 466 in the cavity 426. The airflow blocking elements 466 are arranged so that, when the cartridge 418 is received within the cavity 426, the airflow blocking elements 466 cooperate with the cartridge 418 to direct airflow into the cartridge 418 through the first aperture 436, and then out of the cartridge 418 through the second aperture 438.

Figure 12:
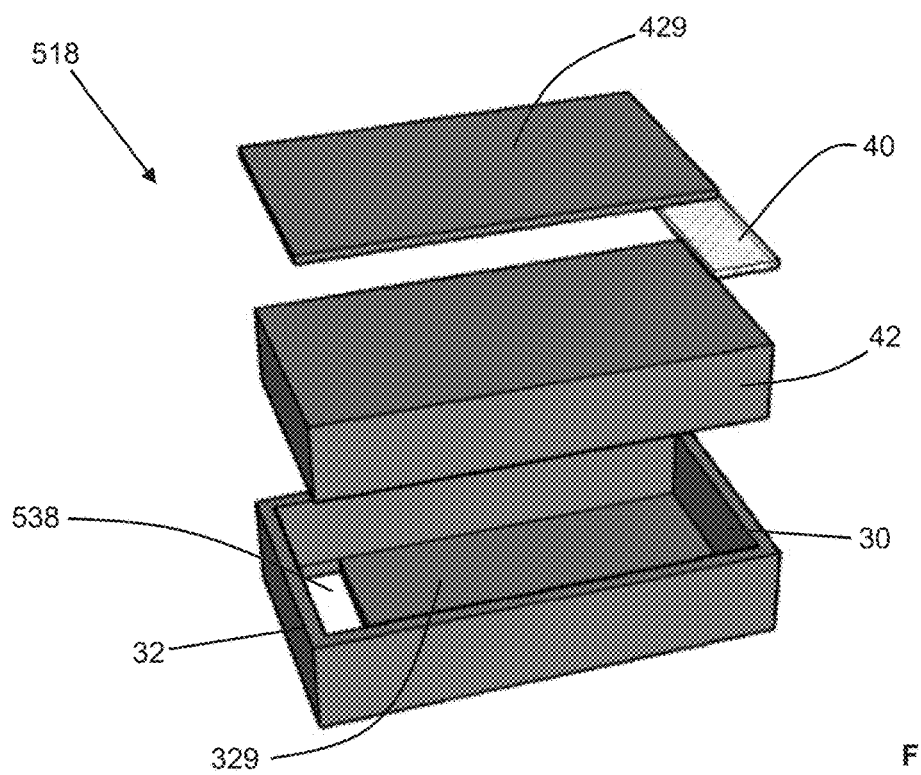
FIG. 12 is an exploded perspective view of another cartridge according to an example embodiment.

FIG. 12 shows a cartridge 518 according to an example embodiment. The cartridge 518 is similar to the cartridge 418 shown in FIGS. 9 and 10 and like reference numerals are used to designate like parts. Cartridge 518 differs by the position of the second aperture 538. In particular, the second aperture 538 is positioned on the second side of the cartridge 518 and adjacent the second end 32.

Figure 13:
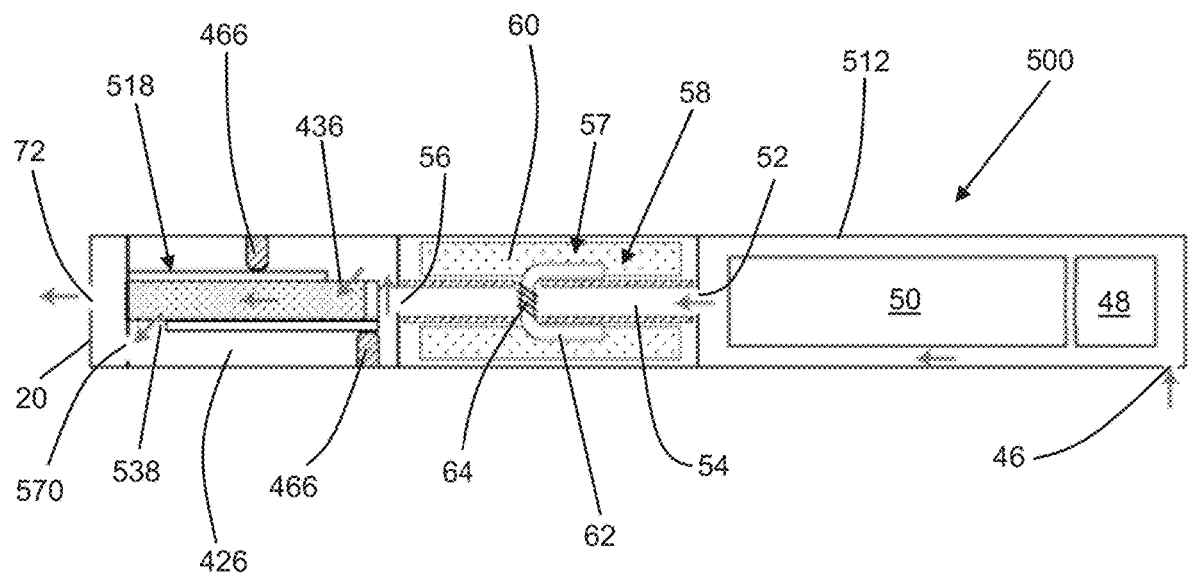
FIG. 13 is a cross-sectional view of an aerosol-generating system comprising the cartridge of FIG. 12.

FIG. 13 shows a cross-sectional view of an aerosol-generating system 500 comprising the cartridge 518 of FIG. 12. The aerosol-generating system 500 is similar to the aerosol-generating system 400 of FIG. 11, and like reference numerals are used to designate like parts.

Aerosol-generating system 500 comprises an aerosol-generating device 512 that is substantially the same as the aerosol-generating device 412 of FIG. 11, except for the position of the cavity air outlet 570.

Figure 14:
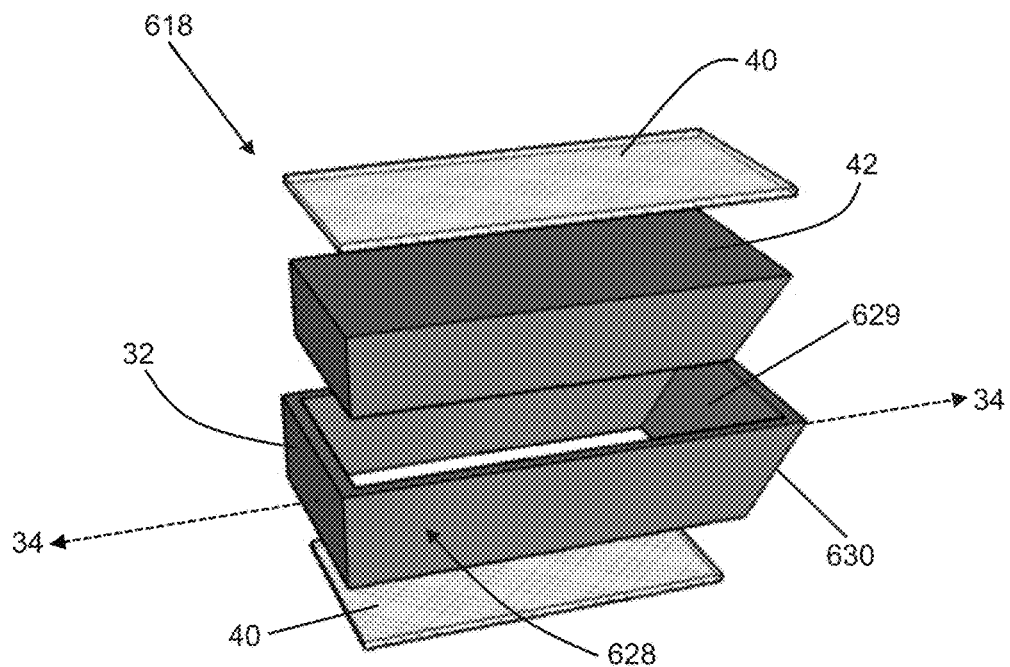
FIG. 14 is an exploded perspective view of another cartridge according to an example embodiment.

FIG. 14 shows a cartridge 618 according to an example embodiment. The cartridge 618 is similar to the cartridge 18 shown in FIGS. 1 to 3 and like reference numerals are used to designate like parts. Cartridge 618 differs by the configuration of the first end 630 of the cartridge 618. In particular, the cartridge housing 628 comprises a wall portion 629 at the first end 630 of the cartridge, wherein the wall portion 629 extends at a non-orthogonal angle with respect to the cartridge axis 34.

Figure 15:
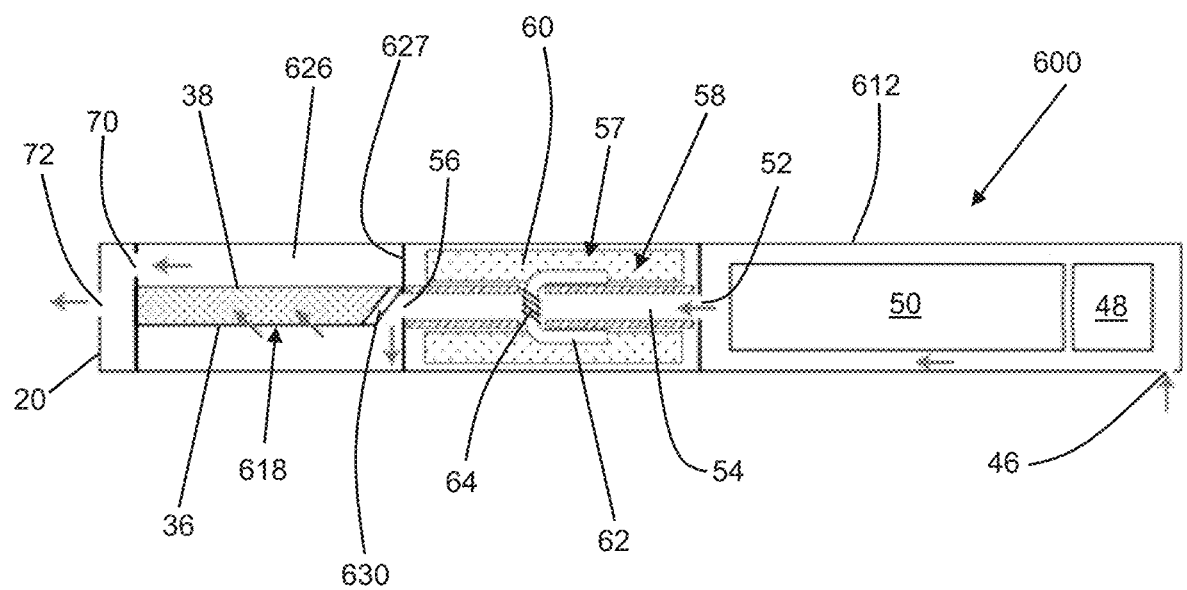
FIG. 15 is a cross-sectional view of an aerosol-generating system comprising the cartridge of FIG. 14.

FIG. 15 shows a cross-sectional view of an aerosol-generating system 600 comprising the cartridge 618 of FIG. 14. The aerosol-generating system 600 is similar to the aerosol-generating system 10 of FIGS. 1 and 3, and like reference numerals are used to designate like parts.

Aerosol-generating system 600 comprises an aerosol-generating device 612 that is substantially the same as the aerosol-generating device 12 of FIGS. 1 and 3, except for the configuration of the cavity 626. In particular, the angled first end 630 of the cartridge 618 eliminates the need for any airflow blocking elements in the cavity 626. Instead, the aerosol-generating system 600 is configured so that, when the cartridge 618 is received within the cavity 626, the angled first end 630 of the cartridge 618 abuts an upstream end wall 627 of the cavity 626. In this configuration, the angled first end 630 of the cartridge 618 directs airflow from the cavity air inlet 56 to the first side of the cartridge 618 where the air flows through the cartridge 618 via the first aperture 36 and the second aperture 38.

Figure 16:
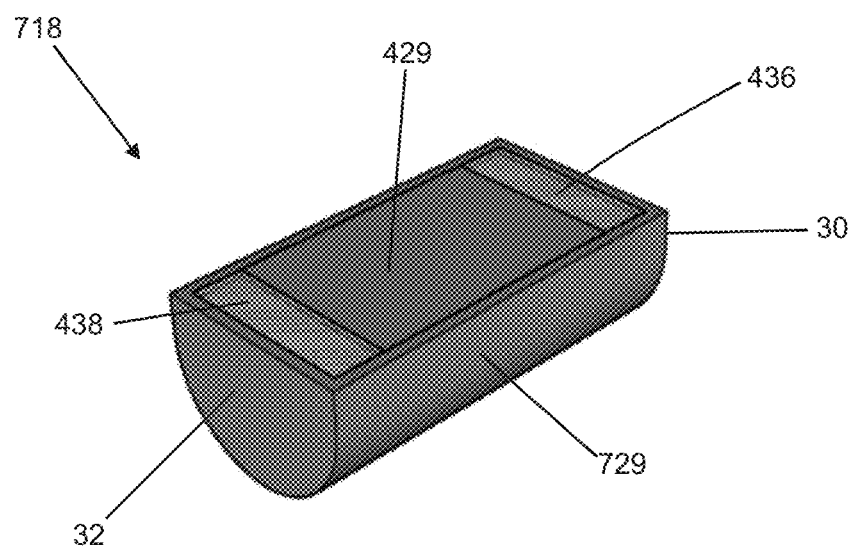
FIG. 16 is a perspective view of another cartridge according to an example embodiment.
Figure 17:
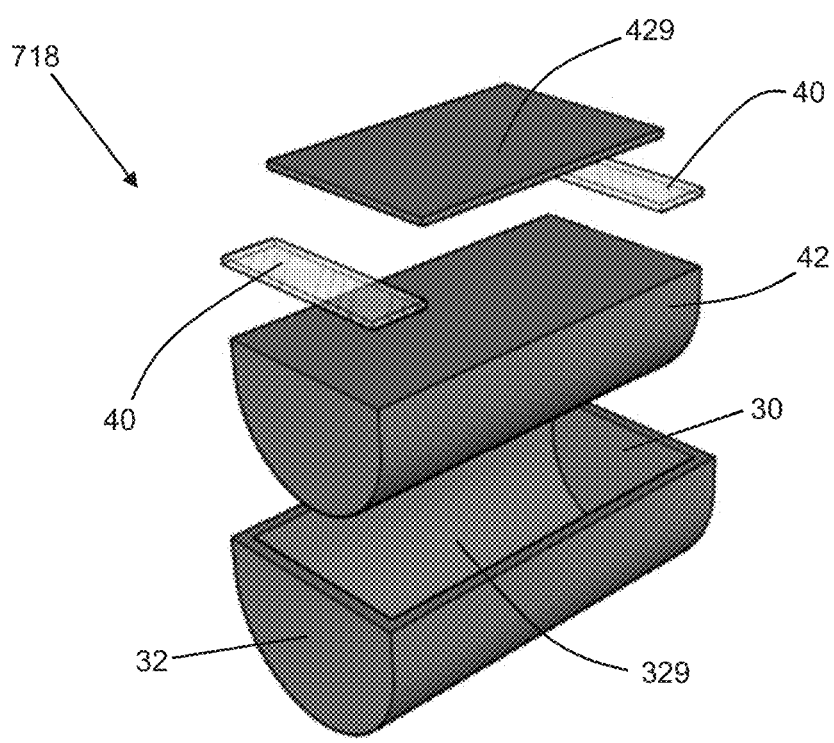
FIG. 17 is an exploded perspective view of the cartridge of FIG. 16.

FIGS. 16 and 17 show a cartridge 718 according to an example embodiment. The cartridge 718 is similar to the cartridge 418 shown in FIGS. 9 and 10 and like reference numerals are used to designate like parts. Cartridge 718 differs by the configuration of the wall portion 729 forming the second side of the cartridge 718. In particular, the wall portion 729 is curved to form a curved second side of the cartridge 718. The cartridge 718 can be used with an aerosol-generating device substantially the same as the aerosol-generating device 412 of FIG. 11, but with a cavity shaped to receive the modified shape of the cartridge 718.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:
1. An aerosol-generating system comprising:
a cartridge including a cartridge housing and a cartridge aerosol-forming substrate within the cartridge housing, the cartridge housing having a first end, a second end, and a cartridge axis extending between the first end and the second end, the cartridge housing defining at least one aperture between the first end and the second end; and
an aerosol-generating device including a device housing, a liquid storage section, an electric heater, and a power supply section, the device housing defining a cavity, a cavity air inlet, and a cavity air outlet, the cavity configured to receive the cartridge, the cavity air inlet at an upstream end of the cavity, the cavity air outlet at a downstream end of the cavity such that an airflow from the cavity air inlet to the cavity air outlet passes through the cartridge via the at least one aperture, the liquid storage section including a liquid aerosol-forming substrate, the electric heater configured to heat the liquid aerosol-forming substrate from the liquid storage section, the power supply section including a power supply and a controller configured to control a supply of electrical power from the power supply to the electric heater,
wherein the cartridge includes a first side and an opposing second side between the first end and the second end, the cartridge aerosol-forming substrate is between the first side and the second side, and the at least one aperture comprises a first aperture on the first side, and
wherein the first end of the cartridge housing extends at a non-perpendicular angle with respect to the cartridge axis, the cartridge and the aerosol-generating device are configured so that a portion of the first end of the cartridge housing abuts an upstream end wall of the cavity when the cartridge is received within the cavity so that the first end of the cartridge housing directs the airflow from the cavity air inlet to the first side of the cartridge.
2. The aerosol-generating system according to claim 1, wherein the first side has a length parallel to the cartridge axis, and the first aperture extends along less than 50 percent of the length of the first side.

3. The aerosol-generating system according to claim 2, wherein the at least one aperture further comprises a second aperture on the first side of the cartridge and spaced apart from the first aperture, the first aperture is proximate to the first end of the cartridge housing, and the second aperture is proximate to the second end of the cartridge housing.

4. The aerosol-generating system according to claim 3, wherein the aerosol-generating device further comprises an airflow blocking element extending inward from a sidewall of the device housing defining the cavity so as to be between the first aperture and the second aperture when the cartridge is received within the cavity, the airflow blocking element configured to direct the airflow from the cavity air inlet through the first aperture, across at least a portion of the cartridge aerosol-forming substrate, and through the second aperture to the cavity air outlet during an operation of the aerosol-generating system.

5. The aerosol-generating system according to claim 3, wherein the at least one aperture further comprises a second aperture on the second side of the cartridge, the first aperture is proximate to the first end of the cartridge housing, and the second aperture is proximate to the second end of the cartridge housing.

6. The aerosol-generating system according to claim 1, wherein the first side has a length parallel to the cartridge axis, and the first aperture extends along at least 50 percent of the length of the first side.

7. The aerosol-generating system according to claim 6, wherein the at least one aperture consists of the first aperture as a sole aperture defined by the cartridge housing.

8. The aerosol-generating system according to claim 7, wherein the aerosol-generating device further comprises an airflow blocking element extending inward from a sidewall of the device housing defining the cavity, the airflow blocking element configured to direct the airflow from the cavity air inlet through the first aperture, across at least a portion of the cartridge aerosol-forming substrate, and back through the first aperture to the cavity air outlet during an operation of the aerosol-generating system.

9. The aerosol-generating system according to claim 6, wherein the at least one aperture further comprises a second aperture on the second side of the cartridge.

10. The aerosol-generating system according to claim 9, wherein the second side has a length parallel to the cartridge axis, the second aperture extends along at least 50 percent of the length of the second side, and the second aperture at least partially overlaps the first aperture.

11. The aerosol-generating system according to claim 1, wherein the at least one aperture further comprises a second aperture on the second side of the cartridge, the cartridge housing defines a plurality of substrate compartments, the cartridge aerosol-forming substrate positioned within at least one of the plurality of substrate compartments, and the plurality of substrate compartments are between the first aperture and the second aperture.

12. The aerosol-generating system according to claim 11, wherein the aerosol-generating device further comprises at least one airflow blocking element extending inward from a sidewall of the device housing defining the cavity, the at least one airflow blocking element configured to direct the airflow from the cavity air inlet along a serpentine path passing through each of the plurality of substrate compartments via the first and second apertures to the cavity air outlet during an operation of the aerosol-generating system.

13. The aerosol-generating system according to claim 1, wherein the cartridge housing includes a curved wall portion defining the second side of the cartridge.

\* \* \* \* \*